United States Patent
Zhang et al.

(10) Patent No.: US 9,593,089 B2
(45) Date of Patent: Mar. 14, 2017

(54) PROCESS FOR PREPARING TDI ISOCYANURATE

(71) Applicants: Wanhua Chemical (Beijing) Co., Ltd., Beijing (CN); Wanhua Chemical Group Co., Ltd., Yantai, Shandong (CN); Wanhua Chemical (Ningbo) Co., Ltd., Ningbo, Zhejiang (CN)

(72) Inventors: Xiao Zhang, Shandong (CN); Yulin Zhu, Shandong (CN); Zhenguang Wen, Shandong (CN); Kai Wang, Shandong (CN)

(73) Assignees: Wanhua Chemical (Beijing) Co., Ltd. (CN); Wanhua Chemical Group Co., Ltd. (CN); Wanhua Chemical (Ningbo) Co., Ltd. (CN)

( * ) Notice: Subject to any disclaimer, the term of this patent is extended or adjusted under 35 U.S.C. 154(b) by 0 days.

(21) Appl. No.: 14/652,242

(22) PCT Filed: Feb. 11, 2014

(86) PCT No.: PCT/CN2014/071951
§ 371 (c)(1),
(2) Date: Jun. 15, 2015

(87) PCT Pub. No.: WO2014/146522
PCT Pub. Date: Sep. 25, 2014

(65) Prior Publication Data
US 2016/0016917 A1    Jan. 21, 2016

(30) Foreign Application Priority Data
Mar. 19, 2013 (CN) .......................... 2013 1 0099777

(51) Int. Cl.
C07D 251/32 (2006.01)
C07D 251/34 (2006.01)
C08G 18/79 (2006.01)
C08G 18/02 (2006.01)
C08G 18/09 (2006.01)

(52) U.S. Cl.
CPC ......... *C07D 251/34* (2013.01); *C08G 18/022* (2013.01); *C08G 18/092* (2013.01)

(58) Field of Classification Search
CPC ........................... C07D 251/32; C07D 251/34
USPC .................................................. 544/221, 193
See application file for complete search history.

(56) References Cited

U.S. PATENT DOCUMENTS

| 5,064,960 A | 11/1991 | Pedain et al. |
| 5,723,564 A | 3/1998 | Schmalstieg et al. |
| 6,028,158 A | 2/2000 | Slack et al. |

FOREIGN PATENT DOCUMENTS

| CN | 1424367 A | 6/2003 |
| CN | 1699353 A | 11/2005 |
| CN | 102911343 A | 2/2013 |
| EP | 2174967 A1 | 4/2010 |

OTHER PUBLICATIONS

CN1699353, Nov. 23, 2005; English Machine Translation provided.*
Jin, Chao et al., "Synthesis and Thermal Stability of a Dimethylbenzene-compatible TDI-trimer" Chinese Journal of Applied Chemistry, No. 6, vol. 22, Jun. 30, 2005, sections 1, 2 and 2, 4.
Zhou, Chengde et al., "Research on the Synthesis of the Toluene Diisocyanate Trimer" Shanghai Coatings, No. 2, Dec. 31, 1998, sections 2 and 3.
International Application No. PCT/CN2014/071951, International Search Report dated May 16, 2014.

* cited by examiner

*Primary Examiner* — Venkataraman Balasubramanian
(74) *Attorney, Agent, or Firm* — Kramer Levin Naftalis & Frankel LLP

(57) ABSTRACT

The present invention relates to a method for preparing TDI (toluene diisocyanate) isocyanurate by using TDI, monohydric alcohol, solvent, antioxidant, catalyst and termination agent as the raw materials. The properties of the isocyanurate are improved by the process comprising the modification by monohydric alcohol and addition of the catalyst and solvent in several stages at an appropriate temperature. By adding the catalyst and solvent in batches at the condition of controlling both NCO % and the viscosity in the preparation process, and adjusting the solid content at each step, the resulting TDI isocyanurate has low content of free TDI, high xylene tolerance, small product color number, and high performance stability, which makes the product obtained by the isocyanurate have good application properties such as the drying, polishing and extinction properties of coating film, and such isocyanurate has good compatibility with other components.

14 Claims, No Drawings

PROCESS FOR PREPARING TDI ISOCYANURATE

FIELD OF THE INVENTION

The present invention relates to a process for preparing TDI (toluene diisocyanate) isocyanurate.

BACKGROUND OF THE INVENTION

Polyisocyanates are the important component of the two-part polyurethane product. The different chemical structures of polyisocyanates have a great impact on the properties of the polyurethane, and the polyisocyanates with isocyanurate heterocyclic structure have the advantages such as low volatility, low toxicity and high functionality. The polyurethanes prepared from isocyanurates have the features of high hardness, resistance to high temperature and the like, and by utilizing isocyanurates in polyurethane coating, the hydrolysis resistance, corrosion resistance, thermal stability and dimensional stability of the resulting polymer can be improved. As a very useful curing agent, isocyanurates can be applied not only to polyurethane systems, but also to the systems containing functional groups such as epoxy resin, poly(meth)acrylate, polyacrylamide, phenol resin, etc. In recent years, the application fields of isocyanurates are widening increasingly at home and abroad, and they have been widely applied in the fields of coating, adhesive, sealant, elastomer, foam plastics and the like.

TDI is the main material for synthesizing isocyanurate curing agent in the polyurethane industry. TDI has relatively high saturated vapor pressure, volatility and toxicity, and harmful to the environment and human health. Since TDI as the raw material has not been reacted completely under given conditions, the resulting TDI isocyanurate still contains a certain amount of free TDI monomers. These free TDI monomers not only lead to waste of resources, but also have a lot of adverse effects on the properties of the paint film such as softening of the paint film, and further are very harmful to the health of the workers and the surrounding environment. Thus, these free TDI monomers must be reduced or recycled. In 2010, China has implemented GB/T18581-2009 "Indoor decorating and refurbishing materials—Limit of harmful substances of solvent based coatings for woodenware", which limits the content of the free TDI monomers in polyurethane coating used for woodenware, wherein the free monomers of the two-part coating after mixing the components at a given ratio are limited to <0.4%, and usually, the main agent:the curing agent:the diluent=2:1:1, thus the standard can be satisfied only when the free TDI % in the curing agent is <1.6%. Therefore, it is important to reduce the free TDI content in the curing agent. Other indexes for evaluating the properties of TDI isocyanurate include color number, xylene tolerance and the like. The smaller the color number of TDI isocyanurate is, the more shallow and high quality of color the paint film can have. The xylene tolerance is defined as the limit for the amount of xylene solvent which can be used to dilute the product without precipitation, which reflects the polarity of the product, i.e., the solubility of the product in the solvent. The higher the xylene tolerance is, the better the compatibility with other components is, and the better the transparency of the resulting paint film is. At present, the domestic TDI isocyanurate products have the platinum-cobalt color number of usually about 30, the xylene tolerance of usually about 1.0, the mass fraction of the free TDI of usually above 1% (based on the solid mass fraction of 50%), whereas the foreign products usually have the mass fraction of the free TDI of usually less than 0.5%. Chinese Patent CN1939949A ("Production of low-free TDI polyurethane curing agent, curing agent therefrom and its products") disclosed the extraction of the remaining free monomer using a phase-transfer solvent, but the reduced pressure distillation requires a lot of energy, which increases the production cost. Chinese Patent CN1699353A ("low-free toluene diisocyanate trimer with high compatibility and preparation process and use thereof") disclosed one-step addition of a solvent and a catalyst. The reaction rate is slow due to the low concentration at the start of the reaction, and thus it is needed to increase the amount of the catalyst, whereas the catalyst may be reacted with oxygen, which leads to the deepening of the color number of the product. Furthermore, the one-step reaction might cause a large difference of the properties (for example the physical properties) such as NCO %, viscosity, tolerance, color and the like between the different batches of the products, and cause a large difference of the application properties such as the drying, polishing and extinction properties of paint film, and the compatibility of such TDI isocyanurate with other components between the different batches of the products, and thus the stability of the different batches of the products is poor.

It is needed to develop a stable and reliable process for preparing TDI isocyanurate having low free TDI content and excellent properties of the final product in the art.

SUMMARY OF THE INVENTION

The object of the present invention is to provide a method for preparing TDI (toluene diisocyanate) isocyanurate. According to the method, isocyanurate is modified using monohydric alcohol, and catalyst and solvent are added in several stages at an appropriate temperature to conduct addition reaction, which makes the concentration of the reactants in the reaction system increased, the reaction rate accelerated, the reaction time shortened, the energy consumption decreased, the amount of the catalyst reduced, and thus the cost reduced. The resulting isocyanurate has an increased compatibility, a reduced color number of the product, and a reduced content of free TDI monomer in the product.

The technical solution of the present invention used to achieve the above-said object is described as below.

Based on the total weight of the all the starting materials, the amount of the starting materials is shown as:

| | |
|---|---|
| Toluene diisocyanate (TDI) | 36~55%, preferably 38~50%, |
| Monohydric alcohol | 0.3~12%, preferably 0.5~10%, |
| Solvent | 41~62%, preferably 48~52%, |
| Antioxidant | 0.1~1%, preferably 0.2~0.5%, |
| Catalyst | 0.03~0.3%, preferably 0.05~0.2%, |
| Termination agent | 0.01~0.2%, preferably 0.02~0.15%. |

The process of synthesizing TDI isocyanurate comprises:
1) The total amount of TDI, the total amount of the antioxidant and the total amount of the monohydric alcohol are placed into a reactor, and thereto a first portion of solvent is added, such that the solid content of the raw materials in the reactor is 59~100%, preferably 80~90%, and the reactor is heated to the temperature of 30~60° C., preferably 50~55° C. and the reaction is conducted for 20~30 min;

2) 60~80% of the total amount of the catalyst is added into the reactor, and the reaction is further conducted at the controlled temperature of 40~70° C., preferably 55~60° C.;

3) When NCO % is 25~30 wt % and the viscosity is ≥200 mPa.s (measured at 25° C.), 10~20% of the total amount of the catalyst and a second portion of solvent are added into the reactor, such that the solid content of the reaction liquid in the reactor is 59~90%, preferably 70~75%, and the reaction temperature is controlled at 40~70° C., preferably 50~65° C.;

4) When NCO % is 13~17 wt % and the viscosity is ≥5000 mPa.s (measured at 25° C.), the remaining portion of the catalyst and a third portion of solvent are added into the reactor, such that the solid content of the reaction liquid in the reactor is 59~75%, preferably 60~65%, and the reaction temperature is controlled at 40~70° C., preferably 50~65° C.;

5) When NCO % is 9~12 wt % and the viscosity is ≥5000 mPa.s (measured at 25° C.), a fourth portion of solvent are added into the reactor, such that the solid content of the reaction liquid in the reactor is 38~59%, preferably 48~52%, and the temperature of the reactor is controlled at 40~70° C., preferably 50~65° C.; and when NCO % is 7.0~8.8 wt %, the termination agent is added, the temperature is lowered to 25~30° C. after stirring for 20~30 min, and then the preparation is completed and the product is discharged.

In the present invention, said toluene diisocyanate (TDI) is chosen from the group consisting of TDI-65 having the molar ratio of toluene-2,4-diisocyanate and toluene-2,6-diisocyanate of 65:35, TDI-80 having the molar ratio of toluene-2,4-diisocyanate and toluene-2,6-diisocyanate of 80:20, TDI-100 consisting of toluene-2,4-diisocyanate or any combination thereof, preferably one or both chosen from TDI-80 and TDI-100. The amount of toluene diisocyanate is 36~55%, preferably 38~50% based on the total weight of the starting materials.

In the present invention, said antioxidant is chosen from the group consisting of Antioxidant 1010 (pentaerythritol tetra[β-(3,5-ditertbutyl-4-hydroxyphenyl)-propionate]), BHT (ditertbutyl-4-methylphenol), triphenyl phosphite, trioctyl phosphite, tridecyl phosphite, and Antioxidant 168 (tri(2,4-ditertbutyl-phenyl) phosphite) or any combination thereof, preferably chosen from pentaerythritol tetra[β-(3,5-ditertbutyl-4-hydroxyphenyl)-propionate]), ditertbutyl-4-methylphenol, triphenyl phosphite, tri(2,4-ditertbutyl-phenyl) phosphite or any combination thereof. The amount of the antioxidant is 0.1~1%, preferably 0.2~0.5% based on the total weight of the starting materials.

In the present invention, said monohydric alcohol is chosen from the group consisting of diethylene glycol monobutyl ether, ethylene glycol monobutyl ether, butyl alcohol, amyl alcohol, octyl alcohol, or any combination thereof, preferably chosen from the group consisting of diethylene glycol monobutyl ether, ethylene glycol monobutyl ether, butanol, or any combination thereof. The amount of the monohydric alcohol is 0.3~12%, preferably 0.5~10% based on the total weight of the raw materials.

In the present invention, said solvent is chosen from the group consisting of ethyl acetate and butyl acetate, alone or mixed in any weight ratio. The amount of the solvent is 41~62%, preferably 48~52% based on the total weight of the raw materials.

In the present invention, said catalyst is chosen from the group consisting of tri(n-butyl) phosphine, triethylene diamine, DMP-30 (2,4,6-tri(dimethylaminomethyl) phenol), BDMA (N,N-dimethyl benzyl amine) and any combination thereof. The amount of the catalyst is 0.03~0.3%, preferably 0.05~0.2% based on the total weight of the raw materials.

In the present invention, said termination agent is chosen from the group consisting of phosphoric acid and benzoyl chloride, alone or mixed in any weight ratio. The amount of the termination agent is 0.01~0.2%, preferably 0.02~0.15% based on the total weight of the raw materials.

The color number (GB/T3143-1982) of the TDI isocyanurate product obtained in the present invention is less than 50, preferably less than 40, more preferably less than 30, particularly preferably less than 20, for example in the range of 10-30 or 15-20. The xylene tolerance of the product is larger than 1.5, preferably larger than 1.6, for example 1.5-5.0, more preferably 2-4.5. NCO % of the product is 5%-10%, preferably 7-8.5%. The free TDI content (GB/T18446-2009) of the product is 0.1-0.9%, preferably 0.2-0.8%, more preferably 0.3-0.7%, or 0.3-0.5%. The viscosity (mPa.s, 25° C.) of the product is 10-90, preferably 20-80.

The xylene tolerance is measured by the method comprising: weighing a certain amount of sample accurately into a dried beaker, adding the xylene solution into the beaker dropwise until white turbid insolubles occurs, and recording the amount of the used xylene. The ratio of the amount of xylene relative to the amount of the sample is the xylene tolerance of the sample.

In the present invention, by the multi-step process comprising modification by monohydric alcohol, the properties of isocyanurate are improved. The advantages of the present invention are as follows:

1. Isocyanurate is urethanized by modifying using monohydric alcohol. Isocyanurate itself is a polar molecule and has a poor compatibility with other molecules, and monohydric alcohol itself is a flexible molecular chain, the flexibility of the isocyanurate segment is increased due to the introduction of monohydric alcohol, and thus xylene tolerance, i.e., the compatibility with the main paint and the solvent is improved and the resulting paint film has a better transparency.

2. The catalyst and solvent are added in several stages, which makes the concentration of the reactants in the reaction system increased, the reaction rate accelerated, and the amount of the catalyst reduced. At the start of the reaction, the proportion of TDI is higher, such that the reaction is well conducted by adding small amount of the catalyst. After reacted to a certain degree, the first portion of the catalyst is encapsulated by the resulting product and the like, causing weakening of the catalytic effect, and at this time, both the viscosity and temperature of the reaction product present in the autoclave are elevated. Thus, the second portion of the solvent is added for reducing the viscosity and temperature, and the second portion of the catalyst is added for continuing the reaction. Such operation is repeated many times to make sure that the reaction be conducted steadily and rapidly, without the temperature and viscosity being too high. After several reactions, toluene diisocyanate monomers are substantially reacted, and the content of free TDI can be reduced to 1.0% or less, or even less than 0.5%.

3. In the course of adding the catalyst and solvent batchwise, a corresponding lower limit of the viscosity is regulated. If the viscosity is too small, the reaction is not enough, so that the overall reaction time is prolonged, and the purpose of saving the reaction time fails to be achieved. If the viscosity is too high, it can result in a sharp increase in temperature and explosive polymerization. Therefore, there is a proper viscosity range in each step, NCO % required to reach said viscosity range is measured, in order to obtain the corresponding range of NCO %. As such, by means of the process of controlling both NCO % and the viscosity, the reaction process is more really and effectively monitored, the time point of adding the solvent and the catalyst is specified explicitly, and the properties such as NCO %, viscosity, tolerance, color and the like of the product produced at every time are more consistent.

4. By reacted at the temperature described in the present invention, the reaction can be conducted smoothly, the product having lighter color and lower color number can be obtained, which has no adverse impact on the final product.

Compared to the prior art, the present invention has the following advantages: the resulting TDI isocyanurate has the free TDI content of <1%, preferably <0.5, xylene tolerance of >1.4, the platinum-cobalt color number of <20, and other physical properties such as NCO %, viscosity, tolerance, color and the like are excellent and stable, which makes the product obtained by the isocyanurate have good application properties such as the drying, polishing and extinction properties of the paint film, and such isocyanurate has good compatibility with other components.

THE MODE OF CARRYING OUT THE INVENTION

The embodiments of the present invention are further described with reference to the Examples. The present invention should not be interpreted to be limited to these examples, rather comprise all variations and modifications within the scope of the claims.

The main raw materials used in the Examples are obtained as follows.
TDI-80: available from BASF, German
TDI-100: available from GANSU YINGUANG CHEMICAL INDUSTRY GROUP CO., LTD.
Toluene: available from Beijing Chemical Works
Butyl acetate: available from JIANGSU HUALUN CHEMICAL INDUSTRY CO., LTD.
Ethyl acetate: available from JIANGSU HUALUN CHEMICAL INDUSTRY CO., LTD.
Sodium phosphite: available from SHANGHAI JIUBANG CHEMICAL CO., LTD.
Triphenyl phosphite: available from Taizhou Sunny Chemical Co., Ltd.
BHT (ditertbutyl-4-methylphenol): available from LANXESS AG, German
Antioxidant 168 ((tri(2,4-ditertbutyl-phenyl) phosphite): available from BASF, German
Antioxidant 1010 (pentaerythritol tetra[β-(3,5-ditertbutyl-4-hydroxyphenyl)-propionate]): available from BASF, German
Diethylene glycol monobutyl ether: available from Tianjin Kemiou Chemical Reagent Co., Ltd.
n-butyl alcohol: available from Beijing Chemical Works
Ethylene glycol monobutyl ether: available from XILONG CHEMICAL CO., LTD.
Tri-n-butyl Phosphine: available from Tokyo Kasei Kogyo Co., Ltd.
Triethylene diamine: available from Tosoh Corporation, Japan
DMP-30: available from Changzhou Shanfeng Chemical Co., Ltd.
BDMA: available from Shanghai Yutian Chemical Co., Ltd.
Benzoyl chloride: available from Beijing Chemical Works

Comparative Example 1

345 g TDI-80, 40 g n-butyl alcohol, 200 g dehydrated butyl acetate, 200 g dehydrated toluene and 4.5 g sodium phosphite are added to a 1000 mL four-necked flask with a stirrer and a thermometer under the protection of nitrogen, stirred homogeneously, heated to 60° C. and reacted for about 1 hour; thereto then is added a mixed solution formed from 0.9533 g DMP-30, 1.9067 g tri-n-butyl phosphine and 80 g dehydrated butyl acetate, and during this time, the variation of NCO % is measured every half hour and the temperature of the reaction system is maintained at about 60° C. When NCO % in the reaction system is decreased to 14.62%, 115 g TDI-80 is added, and further reacted at this temperature. When NCO % in the reaction system is decreased to 8.9%, a mixed solution formed from 0.3072 g benzoyl chloride and 20 g dehydrated butyl acetate is added, the reaction system is heated to 70° C., reacted for about 1 hour, and then lowered to 30° C., and the product is discharged.

Example 1

500 g TDI-80, 14.7 g diethylene glycol monobutyl ether, 80 g ethyl acetate, and 4 g BHT are added to a 1000 mL four-necked flask with a stirrer and a thermometer under the protection of nitrogen such that the solid content is 86.6%, and then stirred homogeneously, heated to 55° C. and reacted for 20 min. Thereto then is added 1.2 g triethylenediamine dropwise slowly, and further reacted. A sample is collected approximately every half an hour to measure the variation of NCO % and viscosity, and the temperature of the reaction system is maintained at about 55° C. When NCO % in the reaction system is decreased to 25.3% and the viscosity is 720 mPa.s (measured at 25° C.), 0.4 g triethylene diamine and 92.8 g ethyl acetate are added such that the solid content is 75%, and further reacted at 55° C. A sample is collected approximately every half an hour to measure the variation of NCO % and viscosity. When NCO % in the reaction system is decreased to 14.1% and the viscosity is 9700 mPa.s (measured at 25° C.), 0.4 g triethylene diamine and 106.8 g ethyl acetate are added such that the solid content is 65%, and further reacted at 55° C. A sample is collected approximately every half an hour to measure the variation of NCO % and viscosity. When NCO % in the reaction system is decreased to 9.3% and the viscosity is 6600 mPa.s (measured at 25° C.), 199.7 g ethyl acetate is added such that the solid content is 52%, and further reacted at 55° C. When NCO % in the reaction system is decreased to 7.62%, 1.5 g benzoyl chloride is added immediately, the temperature is lowered to 25° C. after stirring at 55° C. for 30 min, and then the preparation is completed and the product is discharged.

Example 2

470 g TDI-80, 20 g ethylene glycol monobutyl ether, 80 g ethyl acetate, and 2 g tri(2,4-ditertbutyl-phenyl) phosphite are added to a 1000 mL four-necked flask with a stirrer and a thermometer under the protection of nitrogen such that the solid content is 86.1%, and then stirred homogeneously, heated to 60° C. and reacted for 30 min. Thereto then is added 0.9 g DMP-30 dropwise slowly. A sample is collected approximately every half an hour to measure the variation of NCO % and viscosity, and the temperature of the reaction system is maintained at about 60° C. When NCO % in the reaction system is decreased to 27.8% and the viscosity is 242 mPa.s (measured at 25° C.), 0.2 g DMP-30 and 89 g ethyl acetate are added such that the solid content is 74.5%, and further reacted at 60° C. A sample is collected approximately every half an hour to measure the variation of NCO % and viscosity. When NCO % in the reaction system is decreased to 14.9% and the viscosity is 9000 mPa.s (measured at 25° C.), 0.2 g DMP-30 and 100 g ethyl acetate are added such that the solid content is 64.8%, and further reacted at 60° C. A sample is collected approximately every half an hour to measure the variation of NCO % and viscosity. When NCO % in the reaction system is decreased to 10.1% and the viscosity is 5600 mPa.s (measured at 25° C.), 230 g ethyl acetate is added such that the solid content is 49.9%, and further reacted at 60° C. When NCO % in the reaction system is decreased to 8.21%, 1.0 g phosphoric acid is added immediately, the temperature is lowered to 27° C. after stirring at 60° C. for 30 min, and then the preparation is completed and the product is discharged.

Example 3

470 g TDI-80, 10 g n-butyl alcohol, 10 g ethylene glycol monobutyl ether, 80 g ethyl acetate, and 4 g triphenyl phosphite are added to a 1000 mL four-necked flask with a stirrer and a thermometer under the protection of nitrogen such that the solid content is 86.1%, and then stirred homogeneously, heated to 58° C. and reacted for 25 min; thereto then is added 0.9 g DMP-30 dropwise slowly. A sample is collected approximately every half an hour to measure the variation of NCO % and viscosity, and the temperature of the reaction system is maintained at about 58° C. When NCO % in the reaction system is decreased to 25.7% and the viscosity is 500 mPa.s (measured at 25° C.), 0.2 g DMP-30 and 89 g ethyl acetate are added such that the solid content is 74.5%, and further reacted at 58° C. A sample is collected approximately every half an hour to measure the variation of NCO % and viscosity. When NCO % in the reaction system is decreased to 16.2% and the viscosity is 5060 mPa.s (measured at 25° C.), 0.2 g DMP-30 and 100 g ethyl acetate are added such that the solid content is 64.8%, and further reacted at 58° C. A sample is collected approximately every half an hour to measure the variation of NCO % and viscosity. When NCO % in the reaction system is decreased to 11.0% and the viscosity is 5000 mPa.s (measured at 25° C.), 230 g ethyl acetate is added such that the solid content is 49.9%, and further reacted at 58° C. When NCO % in the reaction system is decreased to 8.24%, 1.2 g benzoyl chloride is added immediately, the temperature is lowered to 30° C. after stirring at 58° C. for 20 min, and then the preparation is completed and the product is discharged.

Example 4

423.2 g TDI-80, 50 g n-butyl alcohol, 47.92 g ethyl acetate, 3 g BHT and 3 g tri(2,4-ditertbutyl-phenyl) phosphite are added to a 1000 mL four-necked flask with a stirrer and a thermometer under the protection of nitrogen such that the solid content is 90%. The reaction system is stirred homogeneously, heated to 60° C. and reacted for 30 min, and then risen to 65° C. Thereto are added 0.3 g DMP-30 and 0.3 g BDMA dropwise slowly. A sample is collected approximately every half an hour to measure the variation of NCO % and viscosity, and the temperature of the reaction system is maintained at about 65° C. When NCO % in the reaction system is decreased to 25.6% and the viscosity is 580 mPa.s (measured at 25° C.), 0.05 g DMP-30, 0.05 g BDMA and 157.75 g ethyl acetate are added such that the solid content is 70%, and further reacted at 65° C. A sample is collected approximately every half an hour to measure the variation of NCO % and viscosity. When NCO % in the reaction system is decreased to 13.0% and the viscosity is 7800 mPa.s (measured at 25° C.), 0.05 g DMP-30, 0.05 g BDMA and 114.33 g ethyl acetate are added such that the solid content is 60%, and further reacted at 65° C. A sample is collected approximately every half an hour to measure the variation of NCO % and viscosity. When NCO % in the reaction system is decreased to 9.4% and the viscosity is 6100 mPa.s (measured at 25° C.), 200 g ethyl acetate is added such that the solid content is 48%, and further reacted at 65° C. When NCO % in the reaction system is decreased to 7.46%, 0.7 g benzoyl chloride is added immediately, the temperature is lowered to 28° C. after stirring at 65° C. for 25 min, and then the preparation is completed and the product is discharged.

Example 5

380 g TDI-100, 100 g n-butyl alcohol, 80 g ethyl acetate, 3 g pentaerythritol tetra[β-(3,5-ditertbutyl-4-hydroxyphenyl)-propionate] and 3 g BHT are added to a 1000 mL four-necked flask with a stirrer and a thermometer under the protection of nitrogen such that the solid content is 85.9%. The reaction system is stirred homogeneously, heated to 40° C. and reacted for 30 min, and thereto is added slowly 0.3 g BDMA dropwise. A sample is collected approximately every half an hour to measure the variation of NCO % and viscosity, and the temperature of the reaction system is maintained at about 40° C. When NCO % in the reaction system is decreased to 25.2% and the viscosity is 200 mPa.s (measured at 25° C.), 0.1 g BDMA and 105.2 g ethyl acetate are added such that the solid content is 72.5%, and further reacted at 40° C. A sample is collected approximately every half an hour to measure the variation of NCO % and viscosity. When NCO % in the reaction system is decreased to 16.1% and the viscosity is 5000 mPa.s (measured at 25° C.), 0.1 g BDMA and 100 g ethyl acetate are added such that the solid content is 63.1%, and further reacted at 40° C. A sample is collected approximately every half an hour to measure the variation of NCO % and viscosity. When NCO % in the reaction system is decreased to 10.6% and the viscosity is 5030 mPa.s (measured at 25° C.), 226 g ethyl acetate is added such that the solid content is 48.8%, and further reacted at 40° C. When NCO % in the reaction system is decreased to 7.82%, 0.2 g benzoyl chloride is added immediately, the temperature is lowered to 25° C. after stirring at 40° C. for 30 min, and then the preparation is completed and the product is discharged.

The properties of the above-said Examples and Comparative Examples are measured, and the results are as shown in table 1. The color number is measured by the platinum-cobalt color number test method (according to GB/T3143-1982 "Color determination method of liquid chemicals"); the viscosity is measured at the condition of 25° C. (measured by using a rotary viscometer); NCO % is measured by the conventional di-n-butylamine titration method (according to GB/T12009.4-1989 "Polymethylene polyphenyl isocyanate-Determination of isocyanato content"); the free TDI % is measured by gas chromatography under normal conditions (according to GB/T18446-2009 "Binders for paints and varnishes—Determination of monomeric diisocyanates in isocyanate resins"); and the measuring method of the xylene tolerance comprises: weighing a certain amount of sample accurately into a dried beaker, adding xylene solution into the beaker dropwise until white turbid insolubles occurs, and recording the amount of the used xylene. The ratio of the amount of xylene relative to the amount of the sample is the xylene tolerance of the sample.

TABLE 1 the test results of the properties of Examples and Comparative Examples samples

| | Reaction time/h | Appearance | Color number | Xylene tolerance | NCO % | Product viscosity (mPa · s) | Free TDI % |
|---|---|---|---|---|---|---|---|
| Comparative example 1 | 14.3 | Red transparent | 80 | 1.37 | 8.90 | 30 | 1.0 |
| Example 1 | 5.7 | Water-white transparent | 15 | 1.57 | 7.62 | 90 | 0.6 |
| Example 2 | 5.9 | Water-white transparent | 20 | 1.52 | 8.21 | 60 | 0.9 |
| Example 3 | 6.3 | Water-white transparent | 15 | 1.58 | 8.24 | 40 | 0.7 |
| Example 4 | 5.1 | Water-white transparent | 15 | 2.91 | 7.46 | 80 | 0.4 |
| Example 5 | 7.4 | Water-white transparent | 15 | 4.31 | 7.82 | 10 | 0.3 |

What is claimed is:

1. A process for preparing TDI isocyanurate, characterized in that said TDI isocyanurate is prepared by addition reaction using TDI, monohydric alcohol, solvent, antioxidant, catalyst and termination agent as the raw materials wherein the catalyst and the solvent are added in several stages, said process comprises:
   1) The total amount of TDI, the total amount of the antioxidant and the total amount of the monohydric alcohol are placed into a reactor, and thereto a first portion of solvent is added, such that the solid content of the raw materials in the reactor is 59~100%, and the reactor is heated to the temperature of 30~60° C. and the reaction is conducted for 20~30 min;
   2) 60~80% of the total amount of the catalyst is added into the reactor, and the reaction is further conducted at the controlled temperature of 40~70° C.;
   3) When NCO % is 25~30 wt % and the viscosity measured at 25° C. is ≥200 mPa.s, 10~20% of the total amount of the catalyst and a second portion of solvent are added into the reactor, such that the solid content of the reaction liquid in the reactor is 59~90%, and the reaction temperature is controlled at 40~70° C.;
   4) When NCO % is 13~17 wt % and the viscosity measured at 25° C. is ≥5000 mPa.s, the remaining portion of the catalyst and a third portion of solvent are added into the reactor, such that the solid content of the reaction liquid in the reactor is 59~75%, and the reaction temperature is controlled at 40~70° C.;
   5) When NCO % is 9~12 wt % and the viscosity measured at 25° C. is ≥5000 mPa.s, a fourth portion of solvent are added into the reactor, such that the solid content of the reaction liquid in the reactor is 38~59%, the reaction temperature is controlled at 40~70° C., and the reaction is continued; and when NCO % is 7.0~8.8 wt %, the termination agent is added, the temperature is lowered to 25~30° C. after stirring for 20~30 min, and then the preparation is completed and the product is discharged.

2. The process as claimed in claim 1, characterized in that said process comprises:
   1) The total amount of TDI, the total amount of the antioxidant and the total amount of the monohydric alcohol are placed into a reactor, and thereto a first portion of solvent is added, such that the solid content of the raw materials in the reactor is 80~90%, and the reactor is heated to the temperature of 50~55° C. and the reaction is conducted for 20~30 min;
   2) 60~80% of the total amount of the catalyst is added into the reactor, and the reaction is further conducted at the controlled temperature of 55~60° C.;
   3) When NCO % is 25~30 wt % and the viscosity measured at 25° C. is ≥200 mPa.s, 10~20% of the total amount of the catalyst and a second portion of solvent are added into the reactor, such that the solid content of the reaction liquid in the reactor is 70~75%, and the reaction temperature is controlled at 50~65° C.;
   4) When NCO % is 13~17 wt % and the viscosity measured at 25° C. is ≥5000 mPa.s, the remaining portion of the catalyst and a third portion of solvent are added into the reactor, such that the solid content of the reaction liquid in the reactor is 60~65%, and the reaction temperature is controlled at 50~65° C.;
   5) When NCO % is 9~12 wt % and the viscosity measured at 25° C. is ≥5000 mPa.s, a fourth portion of solvent are added into the reactor, such that the solid content of the reaction liquid in the reactor is 48~52%, the reaction temperature is controlled at 50~65° C., and the reaction is continued; and when NCO % is 7.0~8.8 wt %, the termination agent is added, the temperature is lowered to 25~30° C. after stirring for 20~30 min, and then the preparation is completed and the product is discharged.

3. The process as claimed in claim 1, characterized in that said TDI is chosen from the group consisting of TDI-65 having the molar ratio of toluene-2,4-diisocyanate and toluene-2,6-diisocyanate of 65:35, TDI-80 having the molar ratio of toluene-2,4-diisocyanate and toluene-2,6-diisocyanate of 80:20, TDI-100 consisting of toluene-2,4-diisocyanate or any combination thereof.

4. The process as claimed in claim 1, characterized in that said antioxidant is chosen from the group consisting of pentaerythritol tetra[β-(3,5-ditertbutyl-4-hydroxyphenyl)-propionate], ditertbutyl-4-methylphenol, triphenyl phosphite, trioctyl phosphite, tridecyl phosphite, and tri(2,4-ditertbutyl-phenyl) phosphite or any combination thereof.

5. The process as claimed in claim 1, characterized in that said solvent is one or two chosen from the group consisting of ethyl acetate and butyl acetate, and the amount of said solvent is 41~62% based on the total weight of the raw materials.

6. The process as claimed in claim 1, characterized in that said catalyst is chosen from the group consisting of tri(n-butyl) phosphine, triethylene diamine, 2,4,6-tri(dimethylaminomethyl) phenol, N,N-dimethyl benzyl amine and any combination thereof, and the amount of said catalyst is 0.03~0.3% based on the total weight of the raw materials.

7. The process as claimed in claim 1, characterized in that said termination agent is one or two chosen from the group consisting of phosphoric acid and benzoyl chloride, and the termination agent is 0.01~0.2% based on the total weight of the raw materials.

8. The process as claimed in claim 1, characterized in that said monohydric alcohol is chosen from the group consisting of diethylene glycol monobutyl ether, ethylene glycol monobutyl ether, butyl alcohol, amyl alcohol, octyl alcohol, or any combination thereof.

9. The process as claimed in claim 1, characterized in that: based on the total weight of the all the starting materials, the amount of the starting materials is shown as:

| | |
|---|---|
| Toluene diisocyanate (TDI) | 36~55% |
| Monohydric alcohol | 0.3~12% |
| Solvent | 41~62% |
| Antioxidant | 0.1~1% |
| Catalyst | 0.03~0.3% |
| Termination agent | 0.01~0.2%. |

10. The process as claimed in claim 3, characterized in that said TDI is one or both chosen from TDI-80 and TDI-100, and the amount of TDI is 36~55% based on the total weight of the starting materials.

11. The process as claimed in claim 4, characterized in that said antioxidant is chosen from pentaerythritol tetra[β-(3,5-ditertbutyl-4-hydroxyphenyl)-propionate]), ditertbutyl-4-methylphenol, triphenyl phosphite, tri(2,4-ditertbutyl-phenyl) phosphite or any combination thereof, and the amount of said antioxidant is 0.1~1% based on the total weight of the starting materials.

12. The process as claimed in claim 8, characterized in that said monohydric alcohol is chosen from the group consisting of diethylene glycol monobutyl ether, ethylene glycol monobutyl ether, butanol, or any combination thereof, and the amount of the monohydric alcohol is 0.3~12% based on the total weight of the raw materials.

13. The process as claimed in claim 9, characterized in that: based on the total weight of the all the starting materials, the amount of the starting materials is shown as:

| | |
|---|---|
| Toluene diisocyanate (TDI) | 38~50%, |
| Monohydric alcohol | 0.5~10%, |
| Solvent | 48~52%, |
| Antioxidant | 0.2~0.5%, |
| Catalyst | 0.05~0.2%, |
| Termination agent | 0.02~0.15%. |

14. TDI isocyanurate prepared by the process of any one of claims 1~9, 10-13, wherein the free TDI content is less than 1% by weight, xylene tolerance is more than 1.4, the platinum-cobalt color number is less than 20, and the viscosity at 25° C. is between 10 and 90 mPa.s.

* * * * *

UNITED STATES PATENT AND TRADEMARK OFFICE
CERTIFICATE OF CORRECTION

| | | |
|---|---|---|
| PATENT NO. | : 9,593,089 B2 | Page 1 of 1 |
| APPLICATION NO. | : 14/652242 | |
| DATED | : March 14, 2017 | |
| INVENTOR(S) | : Xiao Zhang et al. | |

It is certified that error appears in the above-identified patent and that said Letters Patent is hereby corrected as shown below:

On the Title Page

Please correct the spelling of inventor Yunlin Zhu:

(72) Inventors: Xiao Zhang, Shandong (CN); Yunlin Zhu, Shandong (CN); Zhenguang Wen, Shandong (CN); Kai Wang, Shandong (CN)

Signed and Sealed this
Twelfth Day of September, 2017

Joseph Matal
*Performing the Functions and Duties of the*
*Under Secretary of Commerce for Intellectual Property and*
*Director of the United States Patent and Trademark Office*